United States Patent
Drzewinski et al.

(10) Patent No.: US 11,825,842 B2
(45) Date of Patent: Nov. 28, 2023

(54) QUATERNARY AMINE FORMULATIONS AND USES THEREOF

(71) Applicant: Aurorium Holdings LLC, Indianapolis, IN (US)

(72) Inventors: Michael Drzewinski, Long Valley, NJ (US); Tracey Ross, Netcong, NJ (US)

(73) Assignee: Aurorium Holdings LLC, Indianapolis, IN (US)

( * ) Notice: Subject to any disclaimer, the term of this patent is extended or adjusted under 35 U.S.C. 154(b) by 188 days.

(21) Appl. No.: 16/469,888

(22) PCT Filed: Sep. 29, 2017

(86) PCT No.: PCT/US2017/054425
§ 371 (c)(1),
(2) Date: Jun. 14, 2019

(87) PCT Pub. No.: WO2018/111383
PCT Pub. Date: Jun. 21, 2018

(65) Prior Publication Data
US 2020/0077649 A1    Mar. 12, 2020

Related U.S. Application Data

(60) Provisional application No. 62/435,387, filed on Dec. 16, 2016.

(51) Int. Cl.
| | | |
|---|---|---|
| *A01N 33/12* | (2006.01) | |
| *A01N 25/02* | (2006.01) | |
| *A01N 25/30* | (2006.01) | |
| *A01N 37/10* | (2006.01) | |
| *A61K 8/36* | (2006.01) | |
| *A61K 8/41* | (2006.01) | |
| *A61K 8/46* | (2006.01) | |

(52) U.S. Cl.
CPC ............ *A01N 33/12* (2013.01); *A01N 25/02* (2013.01); *A01N 25/30* (2013.01); *A01N 37/10* (2013.01); *A61K 8/36* (2013.01); *A61K 8/416* (2013.01); *A61K 8/463* (2013.01); *A61K 2800/30* (2013.01); *A61K 2800/524* (2013.01); *A61K 2800/59* (2013.01)

(58) Field of Classification Search
CPC .......... A61K 8/416; A61K 47/26; A61K 8/36; A61K 8/34; A61K 2300/00; A01N 33/12; A01N 65/00
See application file for complete search history.

(56) References Cited

U.S. PATENT DOCUMENTS

| 3,990,991 A | 11/1976 | Gerstein |
| 5,306,489 A * | 4/1994 | Goldberg ................. A61K 8/60 424/47 |
| 5,540,853 A | 7/1996 | Trinh et al. |
| 6,211,238 B1 | 4/2001 | Castillo et al. |
| 9,968,537 B2 | 5/2018 | Sharma et al. |
| 2002/0086039 A1 | 7/2002 | Lee et al. |
| 2002/0165283 A1* | 11/2002 | Lutz ...................... A01N 33/12 514/642 |
| 2009/0232748 A1* | 9/2009 | Capps ...................... A61L 2/18 424/49 |

FOREIGN PATENT DOCUMENTS

| CN | 105744836 A | 7/2016 |
| KR | 20150001021 A | 1/2015 |
| WO | 1997007195 A1 | 2/1994 |
| WO | 1994027436 A1 | 12/1994 |
| WO | 2001007086 A1 | 2/2001 |
| WO | 2003034994 A2 | 5/2003 |
| WO | 2011002929 A1 | 1/2011 |
| WO | 2013148247 A2 | 10/2012 |
| WO | 2013066403 A1 | 5/2013 |
| WO | 2013067150 A2 | 5/2013 |
| WO | 2015138479 A1 | 9/2015 |
| WO | 2016156869 A2 | 10/2016 |
| WO | 2018083675 A1 | 5/2018 |

OTHER PUBLICATIONS

PCT International Search Report & Written Opinion for PCT/US2017/054425, completed on Nov. 16, 2017, 9 pages.

* cited by examiner

*Primary Examiner* — Johann R Richter
*Assistant Examiner* — Danielle Sullivan
(74) *Attorney, Agent, or Firm* — Barnes & Thornburg LLP

(57) ABSTRACT

The present disclosure relates to preservative compositions for and methods of preserving household formulations, such as detergents, or preserving topical cosmetic or toiletry formulations against microbiological contamination or growth. Specifically, the disclosure relates to preservative compositions comprising an effective amount of a quaternary amine compound, an effective amount of an antifungal, and a solvent. Further, the disclosure relates to cosmetic or toiletry formulations comprising such preservative compositions. The disclosure further relates to method of making and using such preservative compositions and such cosmetic or toiletry formulations comprising the same.

18 Claims, No Drawings

QUATERNARY AMINE FORMULATIONS AND USES THEREOF

CROSS-REFERENCE TO RELATED APPLICATIONS

This application is a national stage entry made under 35 U.S.C. § 371 of PCT International Application No. PCT/US2017/054425, filed Sep. 29, 2017, which claims priority to United States Provisional Application No. 62/435,387, filed Dec. 16, 2016, each of which is incorporated herein by reference in its entirety.

TECHNICAL FIELD

The present disclosure relates to preservative compositions for and methods of preserving household formulations, such as detergents, or preserving topical cosmetic or toiletry formulations against microbiological contamination or growth. Specifically, the disclosure relates to preservative compositions comprising an effective amount of a quaternary amine compound, an effective amount of an antifungal, and a solvent. Further, the disclosure relates to cosmetic or toiletry formulations comprising such preservative compositions. The disclosure further relates to method of making and using such preservative compositions and such cosmetic or toiletry formulations comprising the same.

BACKGROUND

Topical cosmetic and toiletry products such as creams, lotions, pastes, shampoos, gels, wipes and liquid soaps, are known in the art to be susceptible to microbial contaminants. The raw materials, packaging, and manufacturing environment for these products are often not sufficiently sterile, such that microbiological contaminants can enter into final products. Shipment and storage of packaged cosmetic or toiletry products in some cases are performed under uncontrolled conditions. In some cases, a cosmetic or toiletry product may be exposed to higher temperatures than recommended which can also accelerate the growth rate of microbes unless a suitably effective antimicrobial component and/or components are incorporated into the formulation. Once product packages are opened, they are subject to further contamination from repeated consumer use. A consumer may notice microbial infestation by the discoloration and/or unpleasant odor of a product, or they might see macroscopic quantities of microorganisms such as mold on the product. Microbial growth can also cause the degradation of chemical and/or active compounds in the cosmetic or toiletry formulation, which can lead to instability of the product and/or emulsion. A product that has been contaminated by microbiological organisms can also lead to user infections once it is applied to the skin, scalp and/or mucous membranes of a human. It is therefore important for manufacturers and marketers of such products to be able to offer products that resist microbial growth and provide a stable and safe product with a long shelf life.

Typically, topical cosmetic or toiletry manufacturers add small amounts of one or more preservative compounds to their formulations to prevent microbial growth. The preferred preservatives may be water-soluble, since typically it is the water phase of a product that is most susceptible to microbial growth. Preferred preservatives have been those that are effective at use levels and provide cost-effectiveness, and that do not cause excessive irritation, a disadvantage that is associated with some preservative compounds. Preferred preservatives have been those that do not adversely affect the aesthetic properties of the formulation such as the odor and the color. Furthermore, it is also desirable that the preservative does not affect the performance attributes and/or activity of the product.

Preservatives must follow the guidelines established by individual national laws and regulations. In most countries, these regulations limit the type of and use-level of preservatives that may be included in a product. In some countries, certain preservatives are permitted only for rinse-off products (such as shower gels) but not for leave-on products (such as skin creams.) Therefore, preferred preservatives would be those that are not wholly prohibited in any country, and which are not restricted to only certain product types.

In recent years, cosmetic or toiletry manufacturers have been severely limited in their choice of preservative agents. One class of biocides that has been highly effective in cosmetic or toiletry products includes formaldehyde donors, such as imidazolidinyl urea, diazolidinyl urea, and DMDM hydantoin. However, many such compounds are considered to be skin irritants and the use of formaldehyde donors is severely restricted by regulations in the EU and Japan. Another class of preservatives includes the isothiazolinones, such as methylisothiazolinone (MIT) which is a preservative used in water-based formulations, such as shampoos, liquid soaps, hand lotions and wet wipes. MIT was recently banned by the European Commission in leave-on cosmetic products, and is expected to be further restricted in rinse-off products. Yet another class of preservatives is para-hydroxybenzoic acids, known as parabens. Preservative blends containing parabens are widely used preservative systems. However, research reports such as Journal of Applied Toxicology [2004, 24, 5] have suggested that parabens are possible human carcinogens.

Likewise, certain household products, such as fabric softeners, dishwashing liquids having a pH below about 7, all-purpose cleaners having a pH below about 7, and the like, are known in the art to be susceptible to microbial contaminants.

Because of the recent challenges to traditional preservatives in topical cosmetic and toiletry products, there exists a need to develop novel, economically-viable preservative products that avoid the use of certain components. Likewise, there is a need to develop novel, economically-viable preservative products to preserve household formulations.

SUMMARY

In one aspect the present disclosure relates to a preservative composition comprising
  a. an effective amount of at least one quaternary amine compound;
  b. an effective amount of at least one antifungal agent; and
  c. a solvent.

In another aspect the present disclosure relates to a topical cosmetic or toiletry composition comprising
  a. a preservative composition according to any one of clauses 1 to 16; and
  b. at least one surfactant.

A method of preserving a cosmetic or toiletry composition comprising
  a. mixing an effective amount of a preservative composition comprising at least one quaternary amine compound; at least one antifungal agent; and a solvent into a cosmetic or toiletry formulation, wherein the a preservative composition is capable of inhibiting the growth of one or more microorganisms; and optionally b. cooling the cosmetic or toiletry formulation prior to the step of mixing; and optionally c. adjusting the pH of the cosmetic or toiletry formulation prior to the step of cooling.

In some embodiments, the quaternary amine compound is selected from the group consisting of cetyl pyridinium chloride, benzyl alkonium chloride (benzalkonium chloride), benzethonium chloride, methylbenzethonium chloride, cetalkonium chloride, cetrimonium chloride or bromide, certmide, dofanium chloride, tetraethylammonium bromide, didecyldimethylammonium chloride, and domiphen bromide.

In some embodiments, the antifungal agent is selected from the group consisting of pentylene glycol, caprylyl glycol, dehydroacetic acid, sodium dehydroacetate, sorbic acid, benzoic acid, trihydroxybenzoic acid, sorbitan caprylate, gluconic acid D-lactone, potassium sorbate, sodium salicylate and caprylyhydroxamic acid.

In some embodiments, the solvent is selected from the group consisting of propylene glycol, 1,3-propandiol, glycerin, hexanediol, pentylene glycol, phenoxyethanol, ethylene glycol and benzyl alcohol.

In some embodiments, the cosmetic or toiletry composition is selected from the group consisting of a cream, a lotion, a paste, a shampoo, a gel, a wipe and a liquid soap.

In some embodiments, the surfactant comprises one or more of an anionic surfactant, an amphoteric surfactant, a non-ionic surfactant, or a cationic surfactant.

In some embodiments, the surfactant comprises an anionic surfactant selected from the group consisting of sodium lauryl ether sulfate, sodium lauryl sulfate, ammonium lauryl sulfate, sodium pareth sulfate, sodium lauroyl lactylate, sodium lauryl sulfoacetate, sodium alkyl ($C_{10}$-$C_{16}$) sulfate and sodium laureth sulfosuccinate In some embodiments, the amphoteric surfactant is selected from a group consisting of cocamidopropyl betaine, sodium cocoampoacetate, capryl/capramidopropyl betaine, cocamidopropyl hydroxysultaine, and sodium cocoamphoproprionate.

In some embodiments, the surfactant comprises a non-ionic surfactant selected from the group consisting of PEG-6 cocamide, lauramide DEA/MEA, Cocamide DEA/MEA, decyl glucoside and alkyl polyglucoside.

In some embodiments, the surfactant comprises a cationic surfactant selected from the group consisting of stearalkonium chloride, olealkonium chloride, dipalmitoylethyl hydroxyethylmonium methosulfate, quaternium-82, a polyquaternium, cetrimonium chloride and PCA ethyl cocoyl arginate.

In some embodiments, the topical cosmetic or toiletry composition further comprises EDTA.

In some embodiments, the preservative composition or the topical cosmetic or toiletry composition is substantially free of methylisothiazolinone.

In some embodiments, the preservative composition or the topical cosmetic or toiletry composition is free of methylisothiazolinone.

Embodiments of the invention are further described by the following enumerated clauses:

1. A preservative composition comprising
   a. an effective amount of at least one quaternary amine compound;
   b. an effective amount of at least one antifungal agent; and
   c. a solvent.

2. The preservative composition of clause 1, wherein the antifungal agent and the quaternary amine compound are in a ratio of about 1.2:1 to about 2.2:1.

3. The preservative composition of clause 1 or 2, wherein the antifungal agent and the quaternary amine compound are in a ratio of about 1.5:1 to about 2:1.

4. The preservative composition of any one of the preceding clauses, wherein the quaternary amine compound is about 10 wt % to about 20 wt % of the preservative composition.

5. The preservative composition of clause 4, wherein the quaternary amine compound is about 12 wt % to about 18 wt % of the preservative composition.

6. The preservative composition of any one of the preceding clauses, wherein the antifungal agent is about 20 wt % to about 35 wt % of the preservative composition.

7. The preservative composition of clause 6, wherein the antifungal agent is about 20 wt % to about 25 wt % of the preservative composition.

8. The preservative composition of any one of the preceding clauses, wherein the solvent is about 45 wt % to about 70 wt % of the preservative composition.

9. The preservative composition of clause 8, wherein the solvent is about 55 wt % to about 64 wt % of the preservative composition.

10. The preservative composition of any one of the preceding clauses, wherein the quaternary amine compound is selected from the group consisting of cetyl pyridinium chloride, benzyl alkonium chloride (benzalkonium chloride), benzethonium chloride, methylbenzethonium chloride, cetalkonium chloride, cetrimonium chloride or bromide, certmide, dofanium chloride, tetraethylammonium bromide, didecyldimethylammonium chloride, and domiphen bromide.

11. The preservative composition of any one of the preceding clauses, wherein the quaternary amine compound is cetyl pyridinium chloride.

12. The preservative composition of any one of the preceding clauses, wherein the antifungal agent is selected from the group consisting of pentylene glycol, caprylyl glycol, dehydroacetic acid, sodium dehydroacetate, sorbic acid, benzoic acid, trihydroxybenzoic acid, sorbitan caprylate, gluconic acid D-lactone, potassium sorbate, sodium salicylate and caprylyhydroxamic acid.

13. The preservative composition of any one of the preceding clauses, wherein the antifungal agent is benzoic acid.

14. The preservative composition of any one of the preceding clauses, wherein the solvent is selected from the group consisting of propylene glycol, 1,3-propandiol, glycerin, hexanediol, pentylene glycol, phenoxyethanol, ethylene glycol and benzyl alcohol.

15. The preservative composition of any one of the preceding clauses, wherein the solvent is propylene glycol.

16. The preservative composition of any one of the preceding clauses, wherein the preservative composition is substantially free of methylisothiazolinone.

17. The preservative composition of any one of the clauses 1-15, wherein the preservative composition is free of methylisothiazolinone.

18. A topical cosmetic or toiletry composition comprising
   a. a preservative composition according to any one of clauses 1 to 16; and
   b. at least one surfactant.

19. The cosmetic or toiletry composition of clause 18, wherein the cosmetic or toiletry composition is selected from the group consisting of a cream, a lotion, a paste, a shampoo, a gel, a wipe and a liquid soap.

20. The cosmetic or toiletry composition of clause 18 or 19, wherein the surfactant comprises one or more of an anionic surfactant, an amphoteric surfactant, a non-ionic surfactant, or a cationic surfactant.

21. The cosmetic or toiletry composition of clause 20, wherein the surfactant comprises an anionic surfactant selected from the group consisting of sodium lauryl ether sulfate, sodium lauryl sulfate, ammonium lauryl sulfate, sodium pareth sulfate, sodium lauroyl lactylate, sodium lauryl sulfoacetate, sodium alkyl ($C_{10}$-$C_{16}$) sulfate and sodium laureth sulfosuccinate.

22. The cosmetic or toiletry composition of clause 21, wherein the anionic surfactant is sodium lauryl ether sulfate.

23. The cosmetic or toiletry composition of clause 20, wherein the surfactant comprises an amphoteric surfactant selected from a group consisting of cocamidopropyl betaine, sodium cocoampoacetate, capryl/capramidopropyl betaine, cocamidopropyl hydroxysultaine, and sodium cocoamphoproprionate.

24. The cosmetic or toiletry composition of clause 20, wherein the surfactant comprises a non-ionic surfactant selected from the group consisting of PEG-6 cocamide, lauramide DEA/MEA, Cocamide DEA/MEA, decyl glucoside and alkyl polyglucoside.

25. The cosmetic or toiletry composition of clause 20, wherein the surfactant comprises a cationic surfactant selected from the group consisting of stearalkonium chloride, olealkonium chloride, dipalmitoylethyl hydroxyethylmonium methosulfate, quaternium-82, a polyquaternium, cetrimonium chloride and PCA ethyl cocoyl arginate.

26. The cosmetic or toiletry composition of any one of clauses 18 to 25, wherein the surfactant is in an amount of about 8 to about 15 wt % of the cosmetic or toiletry composition.

27. The cosmetic or toiletry composition of any one of clauses 18 to 26, wherein the preservative composition is in an amount of about 0.2 wt % to about 2.0 wt % of the cosmetic or toiletry composition.

28. The cosmetic or toiletry composition of any one of clauses 18 to 27, wherein the cosmetic or toiletry composition has a pH in the range of about 4 to about 7.

29. The cosmetic or toiletry composition of any one of clauses 18 to 28, further comprising EDTA in an amount of 0.02 wt % to about 0.3 wt % of the cosmetic or toiletry composition.

30. The method of any one of clauses 18 to 29, wherein the preservative composition is substantially free of methylisothiazolinone.

31. The method of any one of clauses 18 to 29, wherein the preservative composition is free of methylisothiazolinone.

32. A process of preparing a preservative composition comprising
a. mixing at least one quaternary amine compound; at least one antifungal agent; and at least one solvent at a temperature of about 40° C. to about 50° C.

33. The process of clause 32, wherein the antifungal agent and the quaternary amine compound are in a ratio of about 1.2:1 to about 2.2:1.

34. The process of clause 32 or 33, wherein the antifungal agent and the quaternary amine compound are in a ratio of about 1.5:1 to about 2:1.

35. The process of any one of clauses 32 to 33, wherein the quaternary amine compound is about 10 wt % to about 20 wt % of the preservative composition.

36. The process of clause 35, wherein the quaternary amine compound is about 12 wt % to about 18 wt % of the preservative composition.

37. The process of any one of clauses 32 to 36, wherein the antifungal agent is about 20 wt % to about 35 wt % of the preservative composition.

38. The process of clause 37, wherein the antifungal agent is about 20 wt % to about 25 wt % of the preservative composition.

39. The process of any one of clauses 32 to 38, wherein the solvent is about 45 wt % to about 70 wt % of the preservative composition.

40. The process of clause 39, wherein the solvent is about 55 wt % to about 64 wt % of the preservative composition.

41. The process of any one of clauses 32 to 40, wherein the quaternary amine compound is selected from the group consisting of cetyl pyridinium chloride, benzyl alkonium chloride (benzalkonium chloride), benzethonium chloride, methylbenzethonium chloride, cetalkonium chloride, cetrimonium chloride or bromide, certmide, dofanium chloride, tetraethylammonium bromide, didecyldimethylammonium chloride, and domiphen bromide.

42. The process of any one of clauses 32 to 41, wherein the quaternary amine compound is cetyl pyridinium chloride.

43. The process of any one of clauses 32 to 42, wherein the antifungal agent is selected from the group consisting of pentylene glycol, caprylyl glycol, dehydroacetic acid, sodium dehydroacetate, sorbic acid, benzoic acid, trihydroxybenzoic acid, sorbitan caprylate, gluconic acid D-lactone, potassium sorbate, sodium salicylate and caprylyhydroxamic acid.

44. The process of any one of clauses 32 to 43, wherein the antifungal agent is benzoic acid.

45. The process of any one of clauses 32 to 44, wherein the solvent is selected from the group consisting of propylene glycol, 1,3-propandiol, glycerin, hexanediol, pentylene glycol, phenoxyethanol, ethylene glycol and benzyl alcohol.

46. The process of any one of clauses 32 to 45, wherein the solvent is propylene glycol.

47. The process of any one of clauses 32 to 46, wherein the temperature is about 50° C.

48. A method of preserving a cosmetic or toiletry composition comprising
a. mixing an effective amount of a preservative composition of any one of clauses 1 to 17 comprising at least one quaternary amine compound; at least one antifungal agent; and a solvent into a cosmetic or toiletry formulation, wherein the a preservative composition is capable of inhibiting the growth of one or more microorganisms.

49. The method of clause 48, wherein the cosmetic or toiletry formulation is heated to a temperature of about 70° C.

50. The method of clause 48, further comprising
b. cooling the cosmetic or toiletry formulation prior to the step of mixing.

51. The method of clause 50, wherein the cosmetic or toiletry formulation is cooled to a temperature of about 40° C. to about 50° C.

52. The method of any one of clauses 48 to 51, further comprising
c. adjusting the pH of the final cosmetic or toiletry formulation prior to the step of cooling.

53. The method of clause 52, wherein the pH is adjusted to about 4 to about 7.

54. The method of any one of clauses 48 to 53, wherein the one or more microorganisms is selected from the group consisting of *Staphylococcus aureus*, *Escherichia coli*, *Pseudomonas aeruginosa*, *Candida albicans* and *Aspergillus brasiliensis*.

55. The method of any one of clauses 48 to 54, wherein the preservative composition is mixed in an amount of about 0.2 wt % to about 2.0 wt % of the cosmetic or toiletry composition.

56. The method of any one of clauses 48 to 55, wherein the antifungal agent and the quaternary amine compound are in a ratio of about 1.2:1 to about 2.2:1.

57. The method of any one of clauses 48 to 56, wherein the antifungal agent and the quaternary amine compound are in a ratio of about 1.5:1 to about 2:1.

58. The method of any one of clauses 48 to 57, wherein the quaternary amine compound is about 10 wt % to about 20 wt % of the preservative composition.

59. The method of any one of clauses 48 to 58, wherein the quaternary amine compound is about 12 wt % to about 18 wt % of the preservative composition.

60. The method of any one of clauses 48 to 59, wherein the antifungal agent is about 20 wt % to about 35 wt % of the preservative composition.

61. The method of any one of clauses 48 to 60, wherein the antifungal agent is about 20 wt % to about 25 wt % of the preservative composition.

62. The method of any one of clauses 48 to 61, wherein the solvent is about 45 wt % to about 70 wt % of the preservative composition.

63. The method of any one of clauses 48 to 62, wherein the solvent is about 55 wt % to about 64 wt % of the preservative composition.

64. The method of any one of clauses 48 to 63, wherein the quaternary amine compound is selected from the group consisting of cetyl pyridinium chloride, benzyl alkonium chloride (benzalkonium chloride), benzethonium chloride, methylbenzethonium chloride, cetalkonium chloride, cetrimonium chloride or bromide, certmide, dofanium chloride, tetraethylammonium bromide, didecyldimethylammonium chloride, and domiphen bromide.

65. The method of any one of clauses 48 to 64, wherein the quaternary amine compound is cetyl pyridinium chloride.

66. The method of any one of clauses 48 to 55, wherein the antifungal agent is selected from the group consisting of pentylene glycol, caprylyl glycol, dehydroacetic acid, sodium dehydroacetate, sorbic acid, benzoic acid, trihydroxybenzoic acid, sorbitan caprylate, gluconic acid D-lactone, potassium sorbate, sodium salicylate and caprylyhydroxamic acid.

67. The method of any one of clauses 48 to 66, wherein the antifungal agent is benzoic acid.

68. The method of any one of clauses 48 to 67, wherein the solvent is selected from the group consisting of propylene glycol, 1,3-propandiol, glycerin, hexanediol, pentylene glycol, phenoxyethanol, ethylene glycol and benzyl alcohol.

69. The method of any one of clauses 48 to 68, wherein the solvent is propylene glycol.

70. The method of any one of clauses 48 to 69, wherein the preservative composition is substantially free of methylisothiazolinone.

71. The method of any one of clauses 48 to 69, wherein the preservative composition is free of methylisothiazolinone.

DETAILED DESCRIPTION

For the purposes of promoting an understanding of the principles of the present disclosure, reference will now be made to certain embodiments thereof and specific language will be used to describe the same. It will nevertheless be understood that no limitation of the scope of the disclosure is thereby intended, such alterations and further modifications of these embodiments, and such further applications of the principles of the invention as described herein being contemplated as would normally occur to one skilled in the art to which the disclosure relates.

Preservative Compositions

As described herein, one aspect of the present disclosure relates to a preservative composition comprising a. an effective amount of at least one quaternary amine compound; b. an effective amount of at least one antifungal agent; and c. a solvent.

It will be appreciated that as used herein, "quaternary amine compound" refers to such quaternary ammonium compound (a.k.a. quats) as are conventionally known in the art and applicable to the personal care product industry. Such quaternary amine compound can be generally described by the formula $NR_4^+X^-$, wherein each R can be independently substituted or unsubstituted alkyl or substituted or unsubstituted aryl, wherein aryl include both all-carbon aromatic groups (such as phenyl or benzyl) and heteroaromatic groups (such as pyridyl), and $X^-$ is a suitable counter-ion (or anion). Suitable quaternary amine compound classes include, but are not limited to alkyltrimethylammonium bromide, dialkyldimethylammonium bromide, alkyldimethylbenzylammonium chloride, dialkylmethylbenzylammonium chloride, substituted or unsubstituted alkylpyridinium chloride, alkylamidomethylpyridinium chloride, carboalkylpyridinium chloride, alkylquinolinium chloride, alkylisoquinolinium chloride. N,N-alkylmethylpyrollodonium chloride, amidoamine from diethylenetriamine (DETA), Suitable quaternary amine compound include, but are not limited to cetyl pyridinium chloride, benzyl alkonium chloride (benzalkonium chloride), benzethonium chloride, methylbenzethonium chloride, cetalkonium chloride, cetrimonium chloride or bromide, certmide, dofanium chloride, tetraethylammonium bromide, didecyldimethylammonium chloride, and domiphen bromide.

It will be appreciated that as used herein. "antifungal agent" refers to such agents as are conventionally known in the art and applicable to the personal care product industry. Numerous classes of compounds known in the art have been shown to exhibit antifungal properties, such as imidazole antifungals, triazole antifungals, thiazole antifungals, polyene antifungals, allylamine antifungals, echinocandin antifungals, thiocarbamate antifungals, hydroxypyridone antifungals and antifungal acids. In some embodiments, preferred antifungal agents include, but are not limited to antifungal acids, such as dehydroacetic acid, sodium dehydroacetate, sorbic acid, benzoic acid, trihydroxybenzoic acid, sorbitan caprylate, gluconic acid D-lactone, potassium sorbate, sodium salicylate, caprylyhydroxamic acid, boric acid, lactic acid, and the like.

The preservative compositions and formulations described herein can include one or more booster agents, such as pentylene glycol, caprylyl glycol, and the like. One of skill in the art will readily appreciate that the identity of the booster agent can be one of many known in the art. Furthermore, the identity of a booster can be specific to a given formulation.

A solvent useful in connection with the preservative compositions of the present disclosure can be any solvent known to one of skill in the art that is considered safe and applicable in the personal care product industry. Such solvents include, but are not limited to, propylene glycol, 1,3-propandiol, glycerin, hexanediol, pentylene glycol, phenoxyethanol, ethylene glycol and benzyl alcohol. In some preferred embodiments, the solvent can be propylene glycol.

It has been surprisingly discovered that the relative proportions of a quaternary amine compound to an antifungal agent in a solvent, all as described above can impact the balance between antimicrobial activity of the resulting preservative composition and the formulation capability of the resulting preservative composition. In some embodiments, it is advantageous to combine an antifungal agent and a quaternary amine compound in a ratio of about 1:1 to about 4:1 as antifungal agent:quaternary amine compound. It will be further appreciated that the present disclosure includes all possible range values of ratios within the limits described, such as 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1 and 4:1. In some embodiments, the antifungal agent and the quaternary amine compound are in a ratio of about 1.2:1 to about 2.2:1. In some embodiments, the antifungal agent and the quaternary amine compound are in a ratio of about 1.5:1 to about 2:1.

In some embodiments, the preservative compositions described herein can be prepared as a concentrate for use in cosmetic or toiletry formulation production. In some embodiments, concentrates of the preservative compositions described herein can be prepared by first dissolving a quaternary amine compound in a solvent as described herein to provide a base concentrate, and then dissolving an antifungal agent as described herein into the base concentrate to provide a preservative composition. In some embodiments, it can be advantageous to warm the solvent to between about 50° C. to about 70° C. prior to dissolving a quaternary amine compound, while stirring the solvent. In some embodiments, it can be advantageous to warm the base concentrate to between about 50° C. to about 70° C. prior to dissolving an antifungal agent, while stirring the base concentrate. In some embodiments, the order of addition of a quaternary amine compound and an antifungal agent can be the reverse of the above description, such that the antifungal agent can be added to a solvent to provide a base concentrate, followed by adding a quaternary amine compound to the base concentrate to provide a preservative composition. In some embodiments, concentrates of the preservative compositions described herein can be prepared by dissolving a quaternary amine compound and an antifungal agent in a solvent as described herein to provide a preservative composition. In some embodiments, it can be advantageous to warm the solvent to between about 50° C. to about 70° C. prior to dissolving a quaternary amine compound and an antifungal agent, while stirring the solvent.

In some embodiments, the quaternary amine compound can be about 10 wt % to about 20 wt % of the preservative composition. In some embodiments, the quaternary amine compound can be about 10 wt % to about 16 wt % of the preservative composition. It will be further appreciated that the present disclosure includes all possible range values of weight % values of antifungal agent within the limits described, such as 11 wt %, 12 wt %, 13 wt %, 14 wt %, 15 wt %, 16 wt %, 17 wt %, 18 wt % and 19 wt %. It will be appreciated that as used herein, "wt %" or "weight %" means the mass fraction of a composition as is commonly known in the art. The wt %, mass fraction ($w_i$), is the ratio of one substance with mass ($m_i$) to the mass of the total mixture ($m_{tot}$), defined as wt %=$m_i/m_{tot}$. One of skill in the art will appreciate that the sum of all mass fractions is equal to 1 as $$\sum_{i=1}^{N} m_i = m_{tot}; \sum_{i=1}^{N} w_i = 1.$$

In some embodiments, the antifungal agent is about 20 wt % to about 35 wt % of the preservative composition. In some embodiments, the antifungal agent is about 20 wt % to about 25 wt % of the preservative composition. It will be further appreciated that the present disclosure includes all possible range values of weight % values of antifungal agent within the limits described, such as 21 wt %, 22 wt %, 23 wt %, 24 wt %, 25 wt %, 26 wt %, 27 wt %, 28 wt %, 29 wt %, 30 wt %, 31 wt %, 32 wt %, 33 wt % and 34 wt %.

In some embodiments, the solvent is about 45 wt % to about 70 wt % of the preservative composition. In some embodiments, the solvent is about 55 wt % to about 64 wt % of the preservative composition. It will be further appreciated that the present disclosure includes all possible range values of weight % values of solvent within the limits described, such as 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt % and 69 wt %.

In some embodiments, the preservative compositions described herein can be substantially free of methylisothiazolinone. It will be appreciated by one of skill in the art that "substantially free" as used herein means that the amount of methylisothiazolinone is below the minimum amount by weight percent or gross weight allowed by any regulatory agency. By way of non-limiting example, if a regulatory agency allows up to 0.1 wt % of methylisothiazolinone in a personal care product or composition, then "substantially free" for purposes of the present disclosure is less than 0.1 wt %. It will be appreciated that one of skill in the art will understand the limits allowed by regulatory authorities for the use of methylisothiazolinone, and will understand the meets and bounds of "substantially free" based on regulatory requirements commonly known in the art.

In some embodiments, the preservative compositions described herein can be free of methylisothiazolinone. It will be appreciated by one of skill in the art that "free of methylisothiazolinone" as used herein means that the preservative composition does not contain any measurable amount of methylisothiazolinone.

Cosmetic or Toiletry Compositions

As described herein, one aspect of the present disclosure relates to a topical cosmetic or toiletry composition comprising a. a preservative composition as described herein; and b. at least one surfactant. It will be appreciated that the teachings of present disclosure can be applied to many cosmetic or toiletry compositions known in the art. By way of non-limiting examples, preservative composition as described herein can be used in connection with topical cosmetic or toiletry composition such as creams, lotions, pastes, shampoos, gels, wipes, liquid soaps, and the like. In some embodiments, the preservative composition is in an amount of about 0.2 wt % to about 2.0 wt % of the cosmetic or toiletry composition. It will be further appreciated that the present disclosure includes all possible range values of weight % values of solvent within the limits described, such as 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt % and 1.9 wt %.

It will be appreciated that as used herein. "surfactant" refers to such agents as are conventionally known in the art and applicable to the personal care product industry known to lower the surface tension between two liquids or between a liquid and a solid, and that may act as detergents, emulsifiers, foaming agents or dispersants. It will be appreciated by one of skill in the art that numerous surfactants can be used in connection with the present disclosure. For example, in some embodiments, the surfactant comprises one or more anionic surfactant, non-ionic surfactant, or cationic surfactant. Suitable anionic surfactants include but are not limited to sodium lauryl ether sulfate, sodium lauryl sulfate, ammonium lauryl sulfate, sodium pareth sulfate, sodium lauroyl lactylate, sodium lauryl sulfoacetate, sodium alkyl ($C_{10}$-$C_{16}$) sulfate and sodium laureth sulfosuccinate. Suitable non-ionic surfactants include but are not limited to PEG-6 cocamide, lauramide DEA/MEA. Cocamide DEA/MEA, decyl glucoside and alkyl polyglucoside. Suitable cationic surfactants include but are not limited to stearalkonium chloride, olealkonium chloride, dipalmitoylethyl hydroxyethylmonium methosulfate, quaternium-82, a polyquaternium, cetrimonium chloride, lauramidopropyl betaine, cocamidopropyl betaine and PCA ethyl cocoyl arginate.

It will be appreciated that surfactants are typically used in a wide range of concentrations in cosmetic or toiletry compositions and formulations. In some embodiments, the surfactant can be in an amount of about 5 to about 30 wt % of the cosmetic or toiletry composition. In some embodiments, the surfactant can be in an amount of about 8 to about 15 wt % of the cosmetic or toiletry composition.

In some embodiments, the cosmetic or toiletry compositions described herein can be substantially free of methylisothiazolinone. It will be appreciated by one of skill in the art that "substantially free" as used herein means that the amount of methylisothiazolinone is below the minimum amount by weight percent or gross weight allowed by any regulatory agency. By way of non-limiting example, if a regulatory agency allows up to 0.1 wt % of methylisothiazolinone in a personal care product or composition, then "substantially free" for purposes of the present disclosure is less than 0.1 wt %. It will be appreciated that one of skill in the art will understand the limits allowed by regulatory authorities for the use of methylisothiazolinone, and will understand the meets and bounds of "substantially free" based on regulatory requirements commonly known in the art.

In some embodiments, the cosmetic or toiletry compositions described herein can be free of methylisothiazolinone. It will be appreciated by one of skill in the art that "free of methylisothiazolinone" as used herein means that the cosmetic or toiletry composition does not contain any measurable amount of methylisothiazolinone.

It will be appreciated that the cosmetic or toiletry compositions described herein can contain other ingredients known in the art as useful in connection with the production such compositions. Suitable examples of other ingredients include, but are not limited to, moisturizer/conditioner, pearlescent pigments, colorants, fragrance, viscosity adjusters and the like. In some embodiments, it can be advantageous to provide cosmetic or toiletry compositions further comprising ethylenediaminetetraacetic acid (EDTA). In some embodiments, the EDTA can be in an amount of 0.02 wt % to about 0.3 wt % of the cosmetic or toiletry composition. It will be appreciated that the EDTA can be added in any wt % described within the stated range including any subrange therein such as, 0.03 wt %, 0.04 wt %, 0.05 wt %, 0.06 wt %, 0.07 wt %, 0.08 wt %, 0.09 wt %, 0.10 wt %, 0.11 wt %, 0.12 wt %, 0.13 wt %, 0.14 wt %, 0.15 wt %, 0.16 wt %, 0.17 wt %, 0.18 wt %, 0.19 wt %, 0.20 wt %, 0.21 wt %, 0.22 wt %, 0.23 wt %, 0.24 wt %, 0.25 wt %, 0.26 wt %, 0.27 wt %, 0.28 wt %, and 0.29 wt %.

The pH of a cosmetic or toiletry composition can be a factor in formulation development. It is known in the art that the pH of skin is from about 4.0 to about 7.0, with typical values in the range of just below 5 to just above 5, which provides what is known as the "acid mantle." (See, for example, Lambres, H. et al., "Natural skin surface pH is on average below 5, which is beneficial for its resident flora." Int. J. Cosmet. Sci. Vol. 28, Issue 5, pp. 359-70 (October 2006). The acid mantle is a thin oily film, made up of sweat and sebum, which sits on top of the outmost layer of skin and protects skin from bacteria entering. When bacteria are killed by acid they can't damage the skin but if you strip skin of its acidic mantle by using it becomes much easier for bacteria to find its way in. Our skin's natural acidity neutralizes chemicals and bacteria, which is a necessary part of the body's defense system. The acid mantle can become unbalanced with the use of strong alkaline soaps, cleansers and detergents. As a result, the pH of cosmetic or toiletry compositions is an important design factor in the industry, and this design factor poses challenges to the industry.

For example, typical shampoos have a pH of between 4 and 6. Acidic shampoos are the most common type of shampoos. These products typically do not contain soap and their pH is closer to the natural pH of hair. Due to their pH, acidic shampoos do not swell the hair shaft or strip the natural oils. The scales on a hair follicle lay flat at a slightly acidic pH, making the hair feel smooth and look shiny. Gentle shampoo for color-treated hair, for example, aides in bringing hair to its optimal pH level of about 4.5 to help freeze color pigments. This process assists in maintaining color for a longer period of time.

Also by way of example, body wash is typically an emulsion/gel of water and detergent base with added functional ingredients such as moisturizer/conditioner, pearlescent pigments, colorants, fragrance, and the like. Body wash often contains milder surfactant bases than shampoos. In addition to being pH-friendly to the skin (5-6.5), most also contain gentle conditioning agents in the formulation. Body wash typically balances proper detergency against a need to avoid degreasing the skin.

As noted above, the pH requirements of cosmetic or toiletry compositions can create challenges to the industry. Specifically, it is known in the art that the optimum pH for growth of *Aspergillus* is in the range of about 3 to about 7 (See, for example, Shouche, S. et al. "The effect of pH on the growth of floral degrading fungi in vitro." BIONANO FRONTIER, vol. 9, pp. 233-235 (January 2012). It is also known in the art that numerous most bacterial growth occurs in an environment having a pH range between about pH 5.5 and about 7.5. It is also known in the art that most fungi, such as yeast and mold, grow best in an environment having a pH range between about pH 4 and about 6.

As a result, contamination of cosmetic or toiletry compositions can become a problem over time. Thus the preservation of such cosmetic or toiletry compositions can be an important aspect of product design.

In some embodiments, the cosmetic or toiletry composition has a pH in the range of about 4 to about 7. It will be appreciated that the present disclosure includes all possible range values of pH values of the cosmetic or toiletry compositions described herein within the limits described above, such as about 4 to about 7, about 4 to about 6, about 5 to about 7, about 5 to about 6, about 6 to about 7, about 6.5 to about 7, and the like. It will be appreciated that the pH of any of the preservative compositions as described herein or any of the cosmetic or toiletry compositions described herein can be optionally adjusted by the addition of either a base, such as a solution of NaOH or and acid, such as citric acid, that is compatible with the composition.

An exemplary anionic soap composition as described herein is shown in Table 1.

TABLE 1

| Ingredient | wt % | wt % | Phase |
|---|---|---|---|
| Water | 42.1 | 41.8-42.3 | A |
| EDTA | 0.1 | 0.1 | A |
| SLES solution (28%) | 48.35 | 48.35 | B |
| Cocamidopropyl betaine | 7.5 | 7.5 | B |
| Preservative composition | 0.65 | 0.75-1.25 | C |
| 20% NaOH solution | 0.1 (as needed) | (as needed) | D |
| 20% citric acid solution | 0.2 (as needed) | (as needed) | D |
| NaCl | 1.0 (as needed) | 1.0 (as needed) | E |
| Total | 100 | 100 | |

An exemplary process for the manufacture of the anionic soap composition of Table 1 can be provided as follows: 1. Combine Phase A ingredients, with continual mixing, start to heat to 60-70° C.; 2. Add Phase B ingredients, continue mixing and heating to between about 60 and about 70° C. 3. Cool composition to between about 40° C. and about 50° C. and combine the preservative composition of the disclosure. Phase C. 4. Add Phase C to Phase A/B between 40-50° C. with continued mixing. 5. Adjust the final formulation pH to 4-7 with Phase D ingredients; and 6. Adjust viscosity with Phase E ingredient. It can be advantageous to cool the pH adjusted Phase A/B composition of step 3 to about 40° C. to about 50° C. prior to the addition of a preservative composition of the disclosure. It can be advantageous to combine a preservative composition of the disclosure with a portion of the cocamidopropyl betaine for compatibility prior to combining with the pH adjusted Phase A/B composition of step 3.

Household Products

One of skill in the art will appreciate that the preservative compositions described herein can also be applied to household products. It will be appreciated that the identity of household products known in the art for use in connection with the preservative compositions described herein are not particularly limited, except that the household product should have a pH of below about 7. Examples of household products for use in connection with the preservative compositions described herein include, but are not limited to, fabric softeners, dishwashing liquids having a pH below about 7, all-purpose cleaners having a pH below about 7, and the like.

The formulation of household products useful in connection with the present preservative compositions are not particularly limited. The various components described herein in connection with the preservative compositions can also be used in connection with household products as appropriate. It will be appreciated that certain components specific to household products may also be used. For example, household products can include surfactants, such as, sodium dodecylbenzene sulfonate, sodium toluene sulfonate, TEA lauryl sulfate, and the like.

Any of the preservative compositions described herein can be used in connection with a household product. In some embodiments, the disclosure provides for a household products, such as a fabric softener, a dishwashing liquid having a pH below about 7, and an all-purpose cleaner having a pH below about 7 comprising a preservative composition as described herein.

It will be appreciated that as used herein, "a" or "an" carries the meaning of "one or more" in open-ended claims containing the transitional phrase "comprising."

Having described preservative compositions and their use in detail as above, the disclosure will now provide the following examples are for illustrative purposes only. The examples are non-limiting, and are not intended to limit the invention in any way. It will be appreciated by one of skill in the art that modification to the examples provided below are contemplated based on the description and embodiments provided herein.

Example 1: Preparation of Test Samples a. Cetylpyridinium Chloride Based Preservative Composition (High Concentration):

Samples were prepared according to Table 3 for later use in freeze/thaw testing. To prepare samples 1 and 4, the stated wt % of cetylpyridinium chloride (CPC) was added to the stated wt % of water and optionally the stated wt % of 70% aqueous SLES solution, optionally followed by the stated wt % of pH adjuster. To prepare samples 2, 3, 5 and 6, the preservative composition contained in the test compositions were made by mixing the stated wt % of propylene glycol (PG) with the stated wt % of benzoic acid (BA), followed by warming the base concentrate mixture of propylene glycol and benzoic acid to about 50° C., then adding the stated wt % of cetylpyridinium chloride (CPC). The preservative composition was then added to a vial containing the stated wt % of water, optionally the stated wt % of a 70% aqueous SLES solution, and optionally the stated wt % of a 20% NaOH or 20% citric acid solution (pH Adj). In Table 2, all amounts shown as wt % are in grams. Table 3 shows the initial pH and the final pH of each test sample after addition of the pH adjuster.

TABLE 2

| Component | 1 | 2 | 3 | 4 | 5 | 6 |
|---|---|---|---|---|---|---|
| Water | 99.00 | 97.50 | 90.00 | 84.70 | 83.20 | 75.70 |
| SLES (70%) | X | X | X | 14.30 | 14.30 | 14.30 |
| CPC | 1.00 | 1.00 | 1.00 | 1.00 | 1.00 | 1.00 |
| BA | X | 1.50 | 1.50 | X | 1.50 | 1.50 |
| PG | X | X | 7.50 | X | X | 7.50 |
| Total | 100 | 100 | 100 | 100 | 100 | 100 |

TABLE 3

| pH | 1 | 2 | 3 | 4 | 5 | 6 |
|---|---|---|---|---|---|---|
| Initial | 6 | 3 | 3 | 8 | 4 | 4 |
| Final | 6 | 6 | 6 | 6 | 6 | 6 | b. Cetylpyridinium Chloride Based Preservative Composition (Low Concentration):

Samples were prepared according to Table 5 for later use in freeze/thaw testing and/or in biological testing. To prepare samples 7, 9, 11 and 13, the stated wt % of cetylpyridinium chloride (CPC) was added to the stated wt % of water and optionally the stated wt % of 70% aqueous SLES solution, optionally followed by the stated wt % of pH adjuster. To prepare samples 8, 10, 12 and 14, the stated wt % of propylene glycol (PG) with the stated wt % of cetylpyridinium chloride (CPC), followed by warming the base concentrate mixture of propylene glycol and benzoic acid to about 50° C., then adding the stated wt % of benzoic acid (BA). The preservative composition was then added to a vial containing the stated wt % of water, the stated wt % of additional propylene glycol, optionally the stated wt % of a 70% aqueous SLES solution, and optionally 20% NaOH or 20% citric acid solution (pH Adj), as needed. In Table 4, all amounts shown as wt % are in grams. Table 5 shows the initial pH and the final pH of each test sample after addition of the pH adjuster.

TABLE 4

| Component | 7 | 8 | 9 | 10 | 11 | 12 | 13 | 14 |
|---|---|---|---|---|---|---|---|---|
| Water | 99.75 | 98.55 | 85.45 | 84.25 | 97.5 | 88.50 | 83.20 | 74.70 |
| SLES (70%) | X | X | 14.30 | 14.30 | X | X | 14.30 | 14.30 |
| CPC | 0.10 | 0.10 | 0.10 | 0.10 | 1.00 | 1.00 | 1.00 | 1.00 |
| BA | X | 0.20 | X | 0.20 | X | 1.50 | X | 1.50 |
| PG | 0.15 | 1.15 | 0.15 | 1.15 | 1.50 | 9.00 | 1.50 | 9.00 |
| Total | 100.00 | 100.00 | 100.00 | 100.00 | 100.00 | 100.00 | 100.00 | 100.00 |

TABLE 5

| pH | 7 | 8 | 9 | 10 | 11 | 12 | 13 | 14 |
|---|---|---|---|---|---|---|---|---|
| Initial | 7 | 3 | 9 | 5 | 6 | 4 | 3 | 4 |
| Final | 6 | 6 | 5 | 6 | 6 | 6 | 6 | 6 | a. Benzyl Alkonium Chloride Based Preservative Composition (High Concentration):

Samples were prepared according to Table 7 for later use in freeze/thaw testing. To prepare samples 15 and 18, the stated wt % of benzyl alkonium chloride (BAK) was added to the stated wt % of water and optionally the stated wt % of 70% aqueous SLES solution, optionally followed by the stated wt % of pH adjuster. To prepare samples 16, 17, 19 and 20, the preservative composition contained in the test compositions were made by mixing the stated wt % of propylene glycol (PG) with the stated wt % of benzoic acid (BA), followed by warming the base concentrate mixture of propylene glycol and benzoic acid to about 50° C., then adding the stated wt % of benzyl alkonium chloride (BAK). The preservative composition was then added to a vial containing the stated wt % of water, optionally the stated wt % of a 70% aqueous SLES solution, and optionally the stated wt % of a 20% NaOH or 20% citric acid solution (pH Adj). In Table 6, all amounts shown as wt % are in grams. Table 7 shows the initial pH and the final pH of each test sample after addition of the pH adjuster.

TABLE 6

| Component | 15 | 16 | 17 | 18 | 19 | 20 |
|---|---|---|---|---|---|---|
| Water | 99.00 | 97.50 | 90.00 | 84.70 | 83.20 | 75.70 |
| SLES (70%) | X | X | X | 14.30 | 14.30 | 14.30 |
| BAK | 1.00 | 1.00 | 1.00 | 1.00 | 1.00 | 1.00 |
| BA | X | 1.50 | 1.50 | X | 1.50 | 1.50 |
| PG | X | X | 7.50 | X | X | 7.50 |
| Total | 100 | 100 | 100 | 100 | 100 | 100 |

TABLE 7

| pH | 15 | 16 | 17 | 18 | 19 | 20 |
|---|---|---|---|---|---|---|
| Initial | 6 | 3 | 3 | 8 | 4 | 4 |
| Final | 6 | 6 | 6 | 6 | 6 | 6 |

Example 2: Freeze Thaw Test

Each sample vial as prepared in Example 1 was subjected to a freeze/thaw challenge where the vial was cooled to −10° C. until the sample froze solid, then was allowed to warm to room temperature. The presence of solid in the vial was identified before and after one cycle of freeze/thaw. Results are shown in Table 8.

TABLE 8

| Sample | Before F/T | After F/T |
|---|---|---|
| 1 | None | None |
| 2 | Yes | Yes |
| 3 | None | None |
| 4 | None | Yes |
| 5 | Yes | Yes |
| 6 | None | None |
| 7 | None | None |
| 8 | None | Yes |
| 9 | None | None |
| 10 | None | None |
| 11 | None | None |
| 12 | None | Yes |
| 13 | None | None |
| 14 | None | None |
| 15 | None | None |
| 16 | Yes | Yes |
| 17 | None | None |
| 18 | None | None |
| 19 | Yes | Yes |
| 20 | None | None |

Example 3: Biological Challenge (Test Sample A)

The testing procedure as well as the neutralization efficacy procedure is based upon the "A Method for Preservation Testing of Water-Miscible Personal Care Products M-3," CTFA Microbiology Guidelines, 2007. The baseline testing procedure is based upon the "Determination of the Microbial Content of Cosmetic Products, M-1," CTFA Microbiology Guidelines, 2007.

Test Sample A Preparation

Test Sample A was prepared according to the procedure described in Example 1(a) using 14.3 wt % of 70% aqueous SLES solution, 0.1 wt % CPC, 0.15 wt % propylene glycol, 0.15 wt % benzoic acid, and 85.3 wt % water. The final pH of the sample composition was 5.

Test Sample B Preparation

Test Sample B was prepared according to the procedure described in Example 1(a) using 35 wt % of 28.6% aqueous Sodium Lauryl sulfate (SLS) solution, 0.2 wt % CPC, 0.3 wt % propylene glycol, 0.2 wt % benzoic acid, and 64.3 wt % water. The final pH of the sample composition was 5.

Test Sample B Preparation

Test Sample B was prepared according to the procedure described in Example 1(a) using 14.4 wt % of 70% aqueous SodiumCoceth-30Sulfate solution, 0.2 wt % CPC, 0.2 wt % benzoic acid, 0.3 wt % propylene glycol, 84.9 wt % water. The final pH of the sample composition was 5.

Acceptance Criteria

1) There is at least a 99.9% (3 log) reduction of vegetative bacteria within 7 days following each challenge and no increase for the duration of the test period.

2) There is at least a 90% (1 log) reduction of yeasts and molds within 7 days following each challenge and no increase during the duration of the test period.

Test Organisms

Staphylococcus aureus—ATCC 6538
Escherichia coli—ATCC 8739
Pseudomonas aeruginosa—ATCC 9027
Candida albicans—ATCC 10231
Aspergillus brasiliensis (formerly A. niger)—ATCC 16404

Baseline Test

A 10.02 gram sample was diluted into 90 mL of Dey-Engley Broth (D/E) to create a 1:10 dilution and to neutralize antimicrobial properties of the test material. One (1.0) mL aliquots of the 1:10 dilution were plated in duplicate. One-tenth (0.1) mL aliquots of the 1:10 dilution were also plated to serve as the $10^{-2}$ dilution. Plates were poured with Tryptic Soy Agar (TSA) and Sabouraud Dextrose Agar (SDA) to serve as the baseline Aerobic Plate Count (APC) and Yeast and Mold (YM) counts for the study as shown in Table 9.

TABLE 9

| APC | Yeast | Mold |
|---|---|---|
| $<1.0 \times 10^2$ | $<1.0 \times 10^1$ | $<1.0 \times 10^1$ |

Neutralizer Efficacy Test

Neutralization effectiveness streaks were conducted for each sample with the challenged organism. From the 1:10 and 1:100 product dilutions created above (Baseline Test), one (1.0) mL aliquots of the 1:10 and 1:100 dilutions were plated for the organism to be challenged. Bacterial plates were poured with TSA and allowed to solidify. Yeast and mold plates were poured with SDA and allowed to solidify. Bacterial, yeast, and mold cultures were prepared and adjusted to yield a suspension at approximately $5.0 \times 10^7$ to $1.0 \times 10^8$ CFU/mL and diluted to $1.0 \times 10^3$ CFU/mL and streaked onto the mold plates. Agar control plates of TSA and SDA were poured and streaked in the same manner. Neutralizer Effectiveness was determined by comparing the growth on the sample to the growth on the agar controls for each test organism/pool of organisms. The neutralizer effectiveness test demonstrated that the media used to conduct the study was suitable for neutralizing the preservative system in the sample at the 1:10 dilution for yeast and mold, and 1:100 for bacteria thereby enabling recovery of viable organisms. In Table 10, "Growth*" means growth of the test organism equivalent in both size and number to that of the control, and "Growth**" means growth of the test organism is not equivalent in size and/or number to that of the control.

TABLE 10

| Test Organism | 1:10 Product Dilution | 1:100 Product Dilution |
|---|---|---|
| Staphylococcus aureus | Growth** | Growth* |
| Escherichia coli | Growth* | Growth* |
| Pseudomonas aeruginosa | Growth* | Growth* |
| Candida albicans | Growth* | Growth* |
| Aspergillus brasiliensis | Growth* | Growth* |

Preservative Efficacy Test

An inoculum for each test organism was prepared in 0.85% Saline to approximately $3.0 \times 10^8$ to $5.0 \times 10^8$ CFU/mL for bacteria and $3.0 \times 10^7$ to $5.0 \times 10^7$ CFU/mL for yeasts and mold. Twenty-five (25.0) gram aliquots of sample were created for each of the challenge organisms and inoculated individually at a level of 0.1 mL per 25 gram aliquot of product. One (1.0) gram samples were removed from each aliquot for enumeration at days 1, 3, 7, 14 and 28. Bacterial plates were poured with TSA and incubated at 30-35° C. for 2 days. Yeast and Mold plates were poured with SDA and incubated at 20-25° C. for 5 days. Following incubation, plates were enumerated.

TABLE 11

| Test Organism | Inoculum CFU/mL | Calculated Theoretical Conc. CFU/g | $Log_{10}$ CFU/g |
|---|---|---|---|
| Staphylococcus aureus | $3.5 \times 10^8$ | $1.4 \times 10^6$ | 6.1 |
| Escherichia coli | $7.1 \times 10^8$ | $2.8 \times 10^6$ | 6.4 |
| Pseudomonas aeruginosa | $5.4 \times 10^8$ | $2.2 \times 10^6$ | 6.3 |
| Candida albicans | $1.6 \times 10^8$ | $6.4 \times 10^5$ | 5.8 |
| Aspergillus brasiliensis | $7.4 \times 10^7$ | $3.0 \times 10^5$ | 5.5 |

TABLE 12a

| Test Organism | Day 1 CFU/g | $Log_{10}/g$ | Day 3 CFU/g | $Log10/g$ | Day 7 CFU/g | $Log_{10}/g$ |
|---|---|---|---|---|---|---|
| Staphylococcus aureus | $<1.0 \times 10^2$ | <2.0 | $<1.0 \times 10^2$ | <2.0 | $<1.0 \times 10^2$ | <2.0 |
| Escherichia coli | $<1.0 \times 10^1$ | <1.0 | $<1.0 \times 10^1$ | <1.0 | $<1.0 \times 10^1$ | <1.0 |
| Pseudomonas aeruginosa | $<1.0 \times 10^1$ | <1.0 | $<1.0 \times 10^1$ | <1.0 | $<1.0 \times 10^1$ | <1.0 |
| Candida albicans | $2.4 \times 10^3$ | 3.4 | $<1.0 \times 10^1$ | <1.0 | $<1.0 \times 10^1$ | <1.0 |
| Aspergillus brasiliensis | $2.6 \times 10^4$ | 4.4 | $1.6 \times 10^3$ | 3.2 | $<1.0 \times 10^1$ | <1.0 |

TABLE 12b

| Test Organism | Day 14 CFU/g | Log₁₀/g | Day 28 CFU/g | Log₁₀/g |
|---|---|---|---|---|
| Staphylococcus aureus | <1.0 × 10² | <2.0 | <1.0 × 10² | <2.0 |
| Escherichia coli | <1.0 × 10¹ | <1.0 | <1.0 × 10¹ | <1.0 |
| Pseudomonas aeruginosa | <1.0 × 10¹ | <1.0 | <1.0 × 10¹ | <1.0 |
| Candida albicans | <1.0 × 10¹ | <1.0 | <1.0 × 10¹ | <1.0 |
| Aspergillus brasiliensis | <1.0 × 10¹ | <1.0 | <1.0 × 10¹ | <1.0 |

TABLE 13

| Test Organism | Day 1 Log₁₀ Reduction | Day 3 Log₁₀ Reduction | Day 7 Log₁₀ Reduction | Day 14 Log₁₀ Reduction | Day 28 Log₁₀ Reduction |
|---|---|---|---|---|---|
| Staphylococcus aureus | >4.1 | >4.1 | >4.1 | >4.1 | >4.1 |
| Escherichia coli | >5.4 | >5.4 | >5.4 | >5.4 | >5.4 |
| Pseudomonas aeruginosa | >5.3 | >5.3 | >5.3 | >5.3 | >5.3 |
| Candida albicans | 2.4 | >4.8 | >4.8 | >4.8 | >4.8 |
| Aspergillus brasiliensis | 1.1 | 2.3 | >4.5 | >4.5 | >4.5 |

TABLE 14

| Test Organism | Day 1 % Reduction | Day 3 % Reduction | Day 7 % Reduction | Day 14 % Reduction | Day 28 % Reduction |
|---|---|---|---|---|---|
| Staphylococcus aureus | >99.99% | >99.99% | >99.99% | >99.99% | >99.99% |
| Escherichia coli | >99.999% | >99.999% | >99.999% | >99.999% | >99.999% |
| Pseudomonas aeruginosa | >99.999% | >99.999% | >99.999% | >99.999% | >99.999% |
| Candida albicans | 99.66% | >99.99% | >99.99% | >99.99% | >99.99% |
| Aspergillus brasiliensis | 91.33% | 99.47% | >99.99% | >99.99% | >99.99% |

Example 4: Biological Challenge (Test Sample D)

The testing procedure as well as the neutralization efficacy procedure is based upon the "A Method for Preservation Testing of Water-Miscible Personal Care Products M-3," CTFA Microbiology Guidelines, 2007. The baseline testing procedure is based upon the "Determination of the Microbial Content of Cosmetic Products, M-1," CTFA Microbiology Guidelines, 2007.

Test Sample D Preparation

Test Sample D was prepared according to the procedure described in Example 1(a) using 14.3 wt % of 70% aqueous SLES solution, 0.1 wt % CPC, 0.15 wt % propylene glycol, 0.2 wt % benzoic acid, and 85.25 wt % water. The final pH of the soap composition was 5.

Acceptance Criteria

1) There is at least a 90% (1 log) reduction of yeasts and molds within 7 days following each challenge and no increase during the duration of the test period.

Test Organisms

Aspergillus brasiliensis (formerly A. niger)—ATCC 16404

Baseline Test

A 10.00 gram sample was diluted into 90 mL of Dey-Engley Broth (D/E) to create a 1:10 dilution and to neutralize antimicrobial properties of the test material. One (1.0) mL aliquots of the 1:10 dilution were plated in duplicate. One-tenth (0.1) mL aliquots of the 1:10 dilution were also plated to serve as the 10² dilution. Plates were poured with Sabouraud Dextrose Agar (SDA) to serve as the baseline Mold (YM) counts for the study. (<1.0×10¹).

Neutralizer Efficacy Test

Neutralization effectiveness streaks were conducted for each sample with the challenged organism. From the 1:10 and 1:100 product dilutions created above (Baseline Test), one (1.0) mL aliquots of the 1:10 and 1:100 dilutions were plated for the organism to be challenged. Mold plates were poured with SDA and allowed to solidify. Mold cultures were prepared and adjusted to yield a suspension at approximately 5.0×10⁷ to 1.0×10⁸ CFU/mL and diluted to 1.0×10³ CFU/mL and streaked onto the mold plates. Agar control plates SDA were poured and streaked in the same manner. Neutralizer Effectiveness was determined by comparing the growth on the sample to the growth on the agar controls for the test organism. The neutralizer effectiveness test demonstrated that the media used to conduct the study was suitable for neutralizing the preservative system in the sample at the 1:10 dilution for mold thereby enabling recovery of viable mold organisms. In Table 15, "Growth*" means growth of the test organism equivalent in both size and number to that of the control.

TABLE 15

| Test Organism | 1:10 Product Dilution | 1:100 Product Dilution |
|---|---|---|
| Aspergillus brasiliensis | Growth* | Growth* |

Preservative Efficacy Test

An inoculum for the test organism was prepared in 0.85% Saline to approximately 3.0×10⁷ to 5.0×10⁷ CFU/mL for mold. A twenty-five (25.0) gram aliquot of sample was created for the challenge organism and was inoculated at a level of 0.1 mL per 25 gram aliquot of product. One (1.0) gram samples were removed from the aliquot for enumeration at days 3, 7, 14, and 28. Mold plates were poured with SDA and incubated at 20-25° C. for 5 days. Following incubation, plates were enumerated.

TABLE 16

| Test Organism | Inoculum CFU/mL | Calculated Theoretical Conc. CFU/g | Log₁₀ CFU/g |
|---|---|---|---|
| Aspergillus brasiliensis | 1.8 × 10⁸ | 7.2 × 10⁵ | 5.9 |

TABLE 17

| Test Organism | Day 3 CFU/g | $Log_{10}/g$ | Day 7 CFU/g | $Log_{10}/g$ | Day 14 CFU/g | $Log_{10}/g$ | Day 28 CFU/g | $Log_{10}/g$ |
|---|---|---|---|---|---|---|---|---|
| Aspergillus brasiliensis | $2.4 \times 10^4$ | 4.4 | $1.8 \times 10^2$ | 2.3 | $4.0 \times 10^1$ | 1.6 | $1.0 \times 10^1$ | 1.0 |

TABLE 18

| Test Organism | Day 3 % Reduction | Day 7 % Reduction | Day 14 % Reduction | Day 28 % Reduction |
|---|---|---|---|---|
| Aspergillus brasiliensis | 96.67% | 99.9% | 99.99% | 99.99% |

What is claimed is:

1. A preservative composition comprising
   a. a quaternary amine compound comprising cetyl pyridinium chloride, and that is 10 wt % to 20 wt % of the preservative composition;
   b. an antifungal agent comprising benzoic acid, and that is 20 wt % to 35 wt % of the preservative composition, and wherein the antifungal agent does not comprise an imidazole antifungal; and
   c. a solvent comprising propylene glycol, and that is 55 wt % to 64 wt % of the preservative composition,
   wherein the antifungal agent and the quaternary amine compound are in a ratio of about 2:1.

2. The preservative composition of claim 1, wherein the quaternary amine compound is 12 wt % to 18 wt % of the preservative composition.

3. The preservative composition of claim 2, wherein the antifungal agent is 20 wt % to 25 wt % of the preservative composition.

4. The preservative composition of claim 1, wherein the preservative composition is substantially free of methylisothiazolinone.

5. A process of preparing a preservative composition comprising
   a. mixing at least one quaternary amine compound comprising cetyl pyridinium chloride, and that is 10 wt % to 20 wt % of the preservative composition; at least one antifungal agent comprising benzoic acid, and that is 20 wt % to 35 wt % of the preservative composition, and wherein the antifungal agent does not comprise an imidazole antifungal; and at least one solvent comprising propylene glycol, and that is 55 wt % to 64 wt % of the preservative composition, at a temperature of 40° C. to 50° C.

6. A topical cosmetic of
   a. the preservative composition according to claim
   b. at least one surfactant.

7. The cosmetic or toiletry composition of claim 6, wherein the surfactant comprises one or more of an anionic surfactant, an amphoteric surfactant, a non-ionic surfactant, or a cationic surfactant.

8. The cosmetic or toiletry composition of claim 6, wherein the surfactant comprises an anionic surfactant selected from the group consisting of sodium lauryl ether sulfate, sodium lauryl sulfate, ammonium lauryl sulfate, sodium pareth sulfate, sodium lauroyl lactylate, sodium lauryl sulfoacetate, sodium alkyl ($C_{10}$-$C_{16}$) sulfate and sodium laureth sulfosuccinate.

9. The cosmetic or toiletry composition of claim 6, wherein the surfactant comprises an amphoteric surfactant selected from a group consisting of cocamidopropyl betaine, sodium cocoampoacetate, capryl/capramidopropyl betaine, cocamidopropyl hydroxysultaine, and sodium cocoamphoproprionate.

10. The cosmetic or toiletry composition of claim 6, wherein the surfactant comprises a non-ionic surfactant selected from the group consisting of PEG-6 cocamide, lauramide DEA/MEA, Cocamide DEA/MEA, decyl glucoside and alkyl polyglucoside.

11. The cosmetic or toiletry composition of claim 6, wherein the surfactant comprises a cationic surfactant selected from the group consisting of stearalkonium chloride, olealkonium chloride, dipalmitoylethyl hydroxyethylmonium methosulfate, quaternium-82, a polyquaternium, cetrimonium chloride and PCA ethyl cocoyl arginate.

12. The cosmetic or toiletry composition of claim 6, wherein the surfactant is in an amount of 8 to 15 wt % of the cosmetic or toiletry composition.

13. The cosmetic or toiletry composition of claim 12, wherein the preservative composition is in an amount of 0.2 wt % to 2.0 wt % of the cosmetic or toiletry composition.

14. The cosmetic or toiletry composition of claim 13, further comprising; EDTA in an amount of 0.02 wt % to 0.3 wt % of the cosmetic or toiletry composition.

15. The cosmetic or toiletry composition of claim 14, wherein the preservative composition is substantially free of methylisothiazolinone.

16. A method of preserving a cosmetic or toiletry composition comprising
   a. mixing an effective amount of the preservative composition of claim 1 into a cosmetic or toiletry formulation, wherein the a preservative composition is capable of inhibiting the growth of one or more microorganisms.

17. The method of claim 16, wherein the one or more microorganisms is selected from the group consisting of Staphylococcus aureus, Escherichia coli, Pseudomonas aeruginosa, Candida albicans and Aspergillus brasiliensis.

18. The method of claim 16, wherein the preservative composition is substantially free of methylisothiazolinone.

* * * * *